United States Patent [19]

Wheatley et al.

[11] Patent Number: 4,693,896
[45] Date of Patent: Sep. 15, 1987

[54] ETHYLCELLULOSE-COATED, GASTRIC-DISINTEGRABLE ASPIRIN TABLET

[75] Inventors: Thomas A. Wheatley, Richboro, Pa.; Rashminkumar S. Shah, East Windsor, N.J.

[73] Assignee: FMC Corporation, Philadelphia, Pa.

[21] Appl. No.: 785,317

[22] Filed: Oct. 7, 1985

[51] Int. Cl.⁴ ............................................. A61K 9/36
[52] U.S. Cl. ......................................... 424/480; 427/3
[58] Field of Search ....................... 424/35, 480; 427/3

[56] References Cited

U.S. PATENT DOCUMENTS

| | | | |
|---|---|---|---|
| 2,881,085 | 4/1959 | Endicott et al. | 424/35 |
| 2,887,440 | 5/1959 | Greminger et al. | 424/35 |
| 3,096,248 | 7/1963 | Rudzki | 424/35 |
| 3,155,590 | 11/1964 | Miller et al. | 167/83 |
| 3,341,416 | 9/1967 | Anderson et al. | 167/83 |
| 3,371,015 | 2/1968 | Sjogren et al. | 424/32 |
| 3,420,931 | 1/1969 | Daum et al. | 424/35 |
| 3,476,588 | 11/1969 | Pitel | 424/35 |
| 3,538,214 | 11/1970 | Polli et al. | 424/35 |
| 3,539,380 | 11/1970 | Johnson | 424/35 |
| 4,017,647 | 4/1977 | Ohno et al. | 427/3 |
| 4,101,651 | 7/1978 | Kobayashi et al. | 424/35 |
| 4,302,440 | 11/1981 | John et al. | 424/35 |
| 4,508,702 | 4/1985 | Hsiao | 424/19 |

*Primary Examiner*—Shep K. Rose
*Attorney, Agent, or Firm*—Christopher Egolf

[57] ABSTRACT

A coated aspirin tablet, which is capable of being disintegrated quickly in gastric fluid, containing a thin film of plasticized ethylcellulose. The ethylcellulose thin film coating represents less than about 2 wt % of the coated tablet weight and is the dried residue of an aqueous ethylcellulose dispersion that is spray-coated onto the tablet.

10 Claims, No Drawings

ETHYLCELLULOSE-COATED, GASTRIC-DISINTEGRABLE ASPIRIN TABLET

BACKGROUND OF THE INVENTION

1. Field of the Invention

This invention concerns gastric-disintegrable aspirin that are coated with a thin film of plasticized ethylcellulose.

2. Description of the Prior Art

Coatings for analgesic tablets, such as aspirin, acetominophen and ibuprofen, can serve as any of several functions, e.g., sustained release, enterosoluble, taste-masking, with the coating formulation being tailored to achieve the desired performance objectives.

U.S. Pat. No. 4,302,440 issued to John et al describes easily-swallowed, gastric-disintegrable aspirin tablets thinly coated with plasticized hydroxypropylmethyl cellulose that is applied via an aqueous spray-coating method.

Enterosoluble aspirin tablets are prepared in U.S. Pat. No. 4,107,647 issued to Ohno et al by coating tablets, via an aqueous system, with hydroxypropyl methylcellulose phthalate that is acid treated after coating. Such tablets pass intact through the stomach but become disintegrated in the intestinal tract.

The cellulosic materials typically used in these coating applications are well known as coating agents. Hydroxypropyl methylcellulose is a water-soluble cellulosic that is commonly used for rapidly-soluble coatings, which are readily disintegrable in the stomach. Enterosoluble cellulosics that are popular include cellulose acetate phthalate and hydroxypropyl methylcellulose phthalate.

Ethylcellulose is a water-insoluble polymer that is known to be useful in sustained release applications. U.S. Pat. No. 4,508,702 describes the encapsulation of aspirin crystals or particles with ethylcellulose having a minor component of water-soluble hydroxypropylcellulose. Sustained release aspirin granules are also described in U.S. Pat. No. 3,341,416 issued to Anderson et al and No. 3,155,590 issued to Miller et al, both of which employ ethyl-cellulose as the primary component for forming a rigid seamless protective coat around each aspirin particle.

The present coating invention employs water-insoluble ethylcellulose, conventionally used in sustained release applications, in a manner which provides a rapidly-disintegrable, taste-masking coating for analgesic tablets, that are nevertheless rapidly solubilized or disintegrated.

SUMMARY OF THE INVENTION

In accordance with the present invention, there is provided a coated, rapidly-disintegrable analgesic tablet which comprises an aspirin tablet core coated with a thin film of ethylcellulose polymer containing 10–40 wt % plasticizer based on the film polymer solids, with the thin film constituting less than about 2 wt % of the coated tablet weight. The thin film is preferably not more than about 1 wt % of the coated tablet weight.

The thin film may contain a water-soluble polymer in admixture with the ethylcellulose, but preferably the thin film is essentially free of other polymeric coating components.

The plasticizer is preferably present in the thin film in an amount of 15–35 wt % based on the polymer solids and is desirably selected from the group consisting of propylene glycol, triethyl citrate, tributyl citrate, dibutyl sebacate, triacetin, polyethylene glycol, diethyl phthalate, acetylated monoglycerides, and mixtures of these.

The thin film coating of ethylcellulose is desirably the dried residue of an aqueous dispersion of ethylcellulose spray-coated onto the analgesic tablet core. The thin film most preferably constitutes from 0.5 to 1 wt % of the coated tablet weight.

DETAILED DESCRIPTION

The primary polymer in the thin-film coatings of this invention is ethylcellulose, a water-immiscible of water-insoluble polymer. Because aqueous coating systems are preferred for applying the ethylcellulose coatings of this invention, the ethylcellulose is conveniently used in the form of an aqueous dispersion of finely-divided ethylcellulose particles. A preferred source of ethylcellulose for use in this invention is an aqueus ethylcellulose dispersion marketed by FMC Corporation under the registered trademark Aquacoat.

The ethylcellulose is preferably employed as sole film-forming polymer in these thin-film coatings, being essentially free of other polymeric coating components.

Other polymeric coating components, however, may also be used in combination wih the ethylcellulose. The water-immiscible ethylcellulose is nevertheless the primary coating polymer is such formulations.

The secondary coating polymer, if used, should be substantially water-soluble. Suitable water-soluble polymers include hydroxyethyl cellulose, hydroxypropyl cellulose, hydroxypropyl methylcellulose, polyvinyl pyrrolidone, sodium carboxymethyl cellulose and the like.

The ethylcellulose polymer, with or without a second coating polymer, should be employed with a plasticizer, in an amount of 10–40 wt % and preferably 15–35 wt % based on the weight of the polymer solids.

The plasticizer is desirably selected from the group consisting of propylene glycol, triethyl citrate, tributyl citrate, dibutyl sebacate, triacetin, polyethylene glycol, diethyl phthalate, acetylated monoglycerides and mixtures of these.

The applied film on the analgesic tablet should constitute less than about 2 wt % of the coated tablet weight, more preferably less than 1.5 wt % and most preferably not more than 1 wt % of the coated tablet weight. The thin film coating should be sufficiently thick to constitute at least 0.4 wt % of the coated tablet weight, and most preferably should constitute from 0.5 to 1 wt % of the coated tablet weight.

The analgesic core is aspirin (acetylsalicylic acid) but the invention is suitable for use with ibuprofen and acetominophen. The tablet core may contain excipients, e.g., microcrystalline cellulose, or other pharmaceutically-acceptable components in admixture with the analgesic.

The thin film ethylcellulose coating on the coated analgesic tablets of this invention offers several benefits, while concurrently providing rapid tablet disintegration or dissolution. The thin ethylcellulose coating are clear films that offer the following advantages not obtained with uncoated tablets:

smooth tablet surface that facilitates ingestion
  bitter taste of the analgesic core is masked
  dusting and tablet edge damage are reduced trade logo imprinted on coating has excellent definition water vapor transmission rate is lowered film acts as protective barrier to air, water vapor and heat improved tablet appearance tablet handling in high speed packaging equipment is facilitated.

The following example serves to illustrate the invention.

EXAMPLE

Standard acetylsalicylic acid (ASA) tablets were coated with clear, continuous, smooth and ductile thin films of ethylcellulose using the coating formulations described below.

All of the coating formulations contained ethylcellulose as the sole coating polymer. Several plasticizers are illustrated in the various formulations, at concentrations of from about 24–30 wt % based on the polymer coating solids.

Following conventional tablet coating procedures as described below, coated tablets were prepared having about 1 wt % film coating, based on the coated tablet weight.

COATING FORMULATIONS

| Formulation 1 | Solids | | Suspension | |
| --- | --- | --- | --- | --- |
| Components | Wt (gm) | Wt % | Wt (gm) | Wt % |
| Aquacoat ® ethylcellulose dispersion | 230 | 76 | 719 | 43 |
| Triacetin plasticizer | 35 | 12 | 35 | 2 |
| Propylene glycol plasticizer | 35 | 12 | 35 | 2 |
| Tween ® 80 surfactant | 2 | 1 | 2 | 1 |
| Water (not including Aquacoat) | — | — | 884 | 53 |
| | 302 | 100 | 1,675 | 100 |

| Formulation 2 | Solids | | Suspension | |
| --- | --- | --- | --- | --- |
| Components | Wt (gm) | Wt % | Wt (gm) | Wt % |
| Aquacoat ® ethylcellulose dispersion | 225 | 80 | 703 | 45 |
| Tributyl citrate (Citroflex ®-4) plasticizer | 54 | 19 | 54 | 3 |
| Tween ® 80 surfactant | 2 | 1 | 2 | 1 |
| Water (not including Aquacoat) | — | — | 804 | 51 |
| | 281 | 100 | 1,563 | 100 |

| Formulation 3 | Solids | | Suspension | |
| --- | --- | --- | --- | --- |
| Components | Wt (gm) | Wt % | Wt (gm) | Wt % |
| Aquacoat ® ethylcellulose dispersion | 240 | 80 | 750 | 45 |
| Dibutyl sebacate (Uniflex ® DBS) plasticizer | 58 | 19 | 58 | 3 |
| Tween ® 80 surfactant | 2 | 1 | 2 | 1 |
| Water (not including Aquacoat) | — | — | 857 | 51 |
| | 300 | 100 | 1,667 | 100 |

| Formulation 4 | Solids | | Suspension | |
| --- | --- | --- | --- | --- |
| Components | Wt (gm) | Wt % | Wt (gm) | Wt % |
| Aquacoat ® ethylcellulose dispersion | 230 | 76 | 742 | 44 |
| Propylene glycol | 35 | 12 | 35 | 2 |
| Dibutyl sebacate (Uniflex ® DBS) plasticizer | 35 | 12 | 35 | 2 |
| Tween ® 80 surfactant | 2 | 1 | 2 | 1 |
| Water (not including Aquacoat) | — | — | 861 | 51 |
| | 302 | 100 | 1,675 | 100 |

PREPARATION OF COATING FORMULATION

1. Tween ® 80 surfactant, used as a dispersing agent, is mixed with the water to dissolve it.
2. The plasticizer is added to the Tween 80/water solution and mixed with mild agitation for five minutes, to dissolve the plasticizer or form an emulsion.
3. The Aquacoat ethylcellulose dispersion is slowly added to the plasticizer/Tween 80/water mixture and mixed for 30–45 minutes using mild shear agitation.
4. Water, as necessary, is added to adjust the final weight to the desired level of solids; 18 wt % solids was used in all coating formulations noted above.

SPRAY COATING EQUIPMENT

Pan: Vector Hi-Coater Model HCT-60
Baffle: 4 kidney shaped; diagonal
Pump: Masterflex peristaltic pump with #7015 heads
Spray gun: Automatic type AT
Fluid cap orifice: 1.2 mm
Air cap orifice: 1.5 mm

SPRAY COATING CONDITIONS

| | Range |
| --- | --- |
| Batch size (kg) | 12 |
| Spray rate (ml/min) | 36–42 |
| Air temperature set (°C.) | 60–79 |
| Air temperature in (°C.) | 58–65 |
| Exhaust temperature (°C.) | 37–45 |
| Atomizing air (std. liters/min) | 120–130 |
| Pattern air (std. liters/min) | 40–60 |
| Control air (kg/cm$^2$) | 5.2 |
| Exhaust air (mm of water) | 190–290 |
| Pan rotation (rpm) | 7–8 |
| Tablet bed warming (min. jogging) | 10 |
| Total coating time (min.) | 30–47 |
| Tablet weight gain (wt. %) | 0.5–1.5 |
| Disintegration (sec.) | 31–44 |
| (Uncoated tablet core disintegration = 26 sec.) | |

We claim:

1. A coated, rapidly-disintegrable analgesic tablet comprising an aspirin tablet core coated with a thin film coating consisting essentially of the dried residue of an aqueous ethylcellulose dispersion that provides a thin film of ethylcellulose polymer containing 10–40 wt % plasticizer based on the film polymer solids, the thin film constituting less than about 2 wt % of the coated tablet weight and consisting essentially of ethylcellulose as the primary coating polymer.

2. The coated tablet of claim 1 wherein the thin film contains a water-soluble polymer in admixture with the ethylcellulose.

3. The coated tablet of claim 2 wherein the water-soluble polymer is selected from the group consisting of hydroxypropyl cellulose, methylcellulose, methylethylcellulose, hydroxypropyl methylcellulose, polyvinylpyrollidone, sodium carboxymethylcellulose.

4. The coated tablet of claim 1 wherein the thin film is essentially free of other polymeric coating components.

5. The coated tablet of claim 1 wherein the tablet core contains excipients or other pharmaceutically-acceptable components in admixture with the analgesic.

6. The coated tablet of claim 1 wherein the plasticizer is present in the thin film in an amount of 15-35 wt % based on the polymer solids.

7. The coated tablet of claim 1 wherein the plasticizer is selected from the group consisting of propylene glycol, triethyl citrate, tributyl citrate, dibutyl sebacate, triacetin, polyethylene glycol diethyl phthalate, acetylated monoglycerides and mixtures of these.

8. The coated tablet of claim 1 wherein the thin film coating constitutes less than 1.5 wt % of the coated tablet weight.

9. The coated tablet of claim 1 wherein the thin film coating constitutes not more than 1 wt % of the coated tablet weight.

10. The coated tablet of claim 1 wherein the thin film coating constitutes from 0.5 to 1 wt % of the coated tablet weight.

* * * * *